United States Patent [19]

Bone

[11] Patent Number: 4,781,922
[45] Date of Patent: Nov. 1, 1988

[54] **CONTROL OF PARASITIC NEMATODE OVA WITH *BACILLUS SPHAERICUS***

[75] Inventor: Leon W. Bone, Auburn, Ala.

[73] Assignee: The United States of America as represented by the Secretary of Agriculture, Washington, D.C.

[21] Appl. No.: 75,168

[22] Filed: Jul. 20, 1987

[51] Int. Cl.⁴ .................. A61K 39/07; A01N 63/00
[52] U.S. Cl. .................................. 424/92; 424/93; 435/832
[58] Field of Search .............. 424/92, 93; 435/832

[56] References Cited

U.S. PATENT DOCUMENTS 4,000,258  12/1976  Shieh et al. ........................ 424/93
4,666,714   5/1987  Cayrol .............................. 424/93
4,713,241  12/1987  Wakisaka et al. ................... 424/93

OTHER PUBLICATIONS

Leon W. Bone et al., "*Trichostrongylus colubriformis*: Larvicidal Activity of Toxic Extracts from *Bacillus sphaerics* (Strain 1593) Spores," Exptl. Parasitol. 64: 514–516 (1987).

H. Ciordia et al., "A Preliminary Report on the Effects of *Bacillus thuringiensis* var. *Thuringiensis* Berliner on the Development of the Free-Living Stages of Some Cattle Nematodes," Abstr. #86, J. Parasitol. 47: 41 (Aug. 1961.).

K. P. Bottjer et al., "Nematoda: Susceptibility of the Egg to *Bacillus thuringiensis* Toxins," Exptl. Parasitol. 60: 239–244 (1985).

R. Tinelli et al., "Isolement d'une Fraction de Spore de *Bacillus sphaericus* Toxique pour les Larves d'Anopheles," C. R. Acad. Sc. Paris, Series D 291: 537–539 (Oct. 13, 1980).

R. Tinelli et al., "Larvicidal Toxin from *Bacillus sphaericus* Spores," FEBS Letters 142(1): 155–158 (Jun. 1982).

*Primary Examiner*—Howard E. Schain
*Attorney, Agent, or Firm*—M. Howard Silverstein; Curtis P. Ribando

[57] ABSTRACT

A method of controlling nematodes in host animals comprising contacting a bacterial extract capable of inhibiting the egg hatching ability of a nematode with said animal and/or its environment. The preferred bacterium for producing the toxin is *Bacillus sphaericus*.

12 Claims, No Drawings

CONTROL OF PARASITIC NEMATODE OVA WITH BACILLUS SPHAERICUS

BACKGROUND OF THE INVENTION

1. Field of the Invention

Typically, high concentrations of anthelmintic compounds are required for killing parasites in their habitat within a host. In the case of intestinal nematodes, anthelmintics must be ingested or absorbed by the worms for expulsion of the parasite from the host. The absorption of the anthelmintic compound by the nematode within the host does not necessarily result in ovicidal activity. Animals being treated are placed in a different pasture or area than before treatment to avoid nematodel ova. There is a need for products which control nematodel ova in the environment of the animal.

This invention relates to a method of controlling nematodes by contacting eggs thereof with a bacterial toxin having ovicidal activity.

2. Description of the Prior Art

Luthy et al. [Pharmacology and Therapeutics 13:257–283 (1981)] teach that various Bacillus species have been recognized as insecticidal pathogens, with *B. thuringiensis* being the most widely used, commercially available bacterium for insect control. According to Burgess [Parasitology 84:79–117 (1982)] a number of isolates of *B. thuringiensis* have been reported. Some of the earlier bacterial varieties were active against lepidopteran insects, more recent isolates of *B. thuringiensis* show activity toward non-lepidopteran insect species. For example, *B. t. israelensis* is active against dipteran insects, such as mosquito species and blackfly larvae. Other varieties of *B. thuringiensis* also show promise against mosquito species which play an important role in the transmission of parasitic diseases of man.

Despite the use of microbial species and their products as insecticides, there is not much information available about the microbial control of nematodes. Ciordia et al. [J. Parisitology 47:abstract 41 (1961)] describe the mixing of spores of *B. thuringiensis* with cow feces that contain eggs of *Cooperia punctata, C. oncophora,* and *Ostertagia ostertagi* and recover reduced numbers of third-stage larvae as the concentration of spores per gram of feces increased clearly showing that some strains of *B. thuringiensis* have nematicidal activity.

Bottjer et al. [Experimental Parisitology 60:239–244 (1985)] teach that a large number of strains of *B. thuringiensis* and their toxins were effective in killing the ruminant nematode *Trichostrongylus colubriformis* and other nematodes. All the tested strains of *B. thuringiensis* were toxic to *T. colubriformis* eggs.

Tinelli et al. [Federation of European Biochemical Societies Letters Vol. 142:155–158 (1982)] suggest that toxins from *Bacillus sphaericus* effectively kill mosquito species, particularly *Anopheles* larvae. Further, Tinelli et al. [CR Acad. Sci. Paris:291/D 537–539 (1980)] describe the technique for the extraction of a crude fraction from *B. sphaericus* Pasteur 1593 spores, which is highly toxic to *An. stephensi* larvae.

SUMMARY OF THE INVENTION

The present invention relates to an exogeneous method of controlling nematodes in host animals comprising treating said animals or their environment with an effective amount of a toxin from the bacterium, *Bacillus sphaericus.* The toxin inhibits the hatchability of nematode eggs. In a typical application of the invention, a sporal extract of the bacterium is combined with a carrier and spread throughout the animal's environment in a manner effective to promote its ovicidal activity.

In accordance with this invention, it is an object of the invention to provide an agent having ovicidal activity against nematodes in a host animal's habitat.

Another object of the present invention is to provide a bacterial extract comprising a toxin having ovicidal activity.

And yet another object of the present invention is to provide means of enhancing the ovicidal activity of a toxin produced by *Bacillus sphaericus.*

Other objects and advantages of this invention will become readily apparent from the following description.

DETAILED DESCRIPTION OF THE INVENTION

This invention relates to an exogeneous method of killing the eggs of a nematode or inhibiting hatchability of nematode eggs by the distribution of a bacterial toxin to the area where the nematode, eggs are found. Thus, the nematode may be controlled, and infection of non-infected animals and re-infection of host animals avoided.

The bacterium, *Bacillus sphaericus,* produces a toxin which has the required ovicidal activity. *B. sphaericus* is a well-known bacterium, and cultures of the bacterium have been placed on deposit with the World Health Organization, Geneva, Switzerland. It is envisioned that most strains of *B. sphaericus* are available for use in accordance with the method of the present invention. The phenomenon of nematode ovicidal control is illustrated by the strain having the WHO accession number WHO/CCBC1593.

In a preferred embodiment of the invention, the toxin may be prepared as a sporal extract from a culture of *B. sphaericus* according to the procedure described in the Tinelli et al. publication [CR Acac. Sci. Paris:291/D 537–539 (1980), herein incorporated by reference]. Alternatively, the toxin may be extracted from the spores of the bacterium *Bacillus sphaericus* and utilized separately for its ovicidal activity.

The bacterial toxin may be distributed or spread throughout an animal's environment—pasture, feedlot, barn, etc. to insure its contact with nematode ova. Preferably, it can be combined with a carrier to facilitate the distribution of the product in the infected animal's environment. The toxin in combination with the carrier should be in an effective amount to be toxic to the eggs or inhibit their hatching under the conditions of administration contemplated by the invention. The carrier may be a liquid which suspends the bacterial product in solution without harmful effects to the toxin for facile spreading or distribution throughout the required area. For example, carriers may be water and oil emulsions, polyhydric alcohols, such as propylene glycol, etc., or lipid materials which may be solid or liquid. Additionally, the carrier may be a dry substance on which the bacterial extract may be absorbed, such as carbohydrate materials, for example, starch granules.

The toxin may also be applied directly to the hide or skin of an animal when combined with a suitable carrier in the form of a liquid drench.

It will be understood that the actual amount of toxin administered will vary depending upon the nematode species, and the environmental conditions, specifically the temperature. The toxin is stable and substantially heat resistant, showing activity in environmental conditions where the temperature is about 75° C. It is also stable over a pH range of about 4.5 to 9.5. Multiple applications may be required in an area to be treated when environmental temperatures are extremely high. It is believed tha the toxin blocks embryonal development of the nematode thereby precluding hatching of the eggs.

Chemical agents or adjuvants may be added to the bacterial extract to increase the ovicidal activity of the toxin. A preferred chemical agent, trypsin, an enzyme, when added to the extract of the bacterium, increases its ovicidal activity 10,000-fold when assayed by dose response (LD50).

The following examples are intended only to further illustrate the invention and are not intended to limit the scope of the invention which is defined by the claims:

EXAMPLE 1

The ruminant nematode *Trichostrongylus colubriformis* was maintained in male, crossbred goats that averaged 20 kg in weight at time of infection. The animals were killed at 21 days after infection and the eggs were removed from rectal feces, surfaces sterilized, and placed in media according to the procedures described by Bottjer et al. supra. A sporal extract of the bacterium *Bacillus sphaericus* WHO/CCBC-1593, was prepared according to the described procedures of Tinelli et al. (1980) supra in which an aqueous spore suspension is successively frozen and thawed nine times. The suspension is then centrifuged at 35,000×g for about 30 minutes. The supernatant is then lyophilized. The sporal extract was placed in reagent-grade water (1 mg/ml) ground with a manual tissue grinder and sonicated for five minutes before testing for ovicidal effects. Preparations were made at various toxin dose levels and total protein/ml was determined for each preparation by Lowrey's procedure. *J. Biol. Chem.*, 193:265 (1951)

The ovicidal activity of *B. sphaericus* sporal extract was determined by placing various doses in the wells of micro titer plates that contain nematode eggs in *Caemorhabditis briggsae* maintenance media supplied by Gibco, Grand Island, N.Y. Sixteen replicates were performed for any dosage while unexposed eggs were used as controls to determine the percentage of larval viability.

Dose response analysis was performed to determine the active range of the extract from *B. sphaericus* for nematode eggs. The sporal extract was tested for ovicidal activity periodically during a 12 day interval of storage at room temperature to assess any activation of toxicity and stability of the toxin. The results are reported in Table I, below.

TABLE I

Ovicidal toxicity of a sporal extract from *B. sphaericus* during the indicated period, based on the larval viability of *Trichostrongylus colubriformis* eggs.

| Time (days) | LD$_{50}$ ($\mu$ total protein/ml) |
|---|---|
| 1 | 0.65 |
| 2 | 0.64 |
| 5 | 0.66 |
| 6 | 0.34 |
| 7 | 3.00 |
| 8 | 2.50 |
| 12 | 7.00 |

EXAMPLE 2

The bacterial sporal extract obtained from the procedure identified in Example 1 was treated with trypsin (10 μg/ml for 72 hours to examine any enzymatic activation or release of the toxin. The trypsin-treated extract was compared to untreated toxin in a larval viability study as described in Example 1.

The results are shown in Table II.

TABLE II

Effect of trypsin treatment on the ovicidal activity of fresh *Bacillus sphaericus* extract as indicated by larval viability.

| Toxin Dosage (μg total protein/ml) | Larval Viability (% ± SEM) | |
|---|---|---|
| | Untreated toxin | Trypsin-treated toxin |
| 0 | 71(±3.8)[a] | 65(±3) |
| 0.00022 | — | 29(±3.6) |
| 0.0022 | 67(±4.3) | 25(±3.3) |
| 0.022 | 73(±5) | 3(±1.5) |
| 0.22 | 64(±3.2) | 0 |
| 2.2 | 0 | 0 |
| 22 | 0 | 0 |

[a]Values in parenthesis represent standard error of the mean.

The method of the present invention may be combined with conventional anthelmintic treatment for complete nematicidal activity. Examples of conventional anthelmintic drugs are morantel tartrate, ivermectin, levamisole, oxfendazole, piperazine citrate, pyrantel pamoate, tetramisole, and thiabendazole.

It is understood that the foregoing detailed description is given merely by way of illustration and that modification and variations may be made therein without departing from the spirit and scope of the invention.

What is claimed is:

1. A method of controlling nematodes in a host animal's environment comprising
   contacting nematode eggs with an effective amount of a toxin from the bacterium *Bacillus sphaericus*, which toxin is capable of inhibiting the egg hatching ability of said nematode.

2. The method as described in claim 1 wherein said toxin is combined with a carrier.

3. The method as described in claim 2 wherein said carrier is selected from the group consisting of water, polyhydric alcohols, water in oil emulsions, lipid materials and carbohydrate materials.

4. The method as described in claim 1 wherein the nematode is *Trichostrongylus colubriformis*.

5. A method of increasing the ovicidal activity of a toxin produced by *Bacillus sphaericus* comprising:
   extracting a toxin having ovicidal activity from said organism, and treating said toxin with a chemical agent to increase its ovicidal activity.

6. The method as described in claim 5 wherein said chemical agent is trypsin.

7. The method as described in claim 5 wherein the increase in ovicidal activity is about 10,000 fold.

8. A method of killing nematode ova comprising:
   contacting said ova with an effective amount of an ovicidal extract from a culture of the bacterium *Bacillus sphaericus*.

9. The method as described in claim 8 wherein said extract is combined with a carrier.

10. The method as described in claim 9 wherein the carrier is selected from the group consisting of water, polyhydric alcohols, water in oil emulsions, lipid materials and carbohydrate materials.

11. The method as described in claim 8 wherein the nematode is *Trichostrongylus colubriformis*.

12. The method as described in claim 1 wherein said toxin comprises a trypsinized sporal extract from the bacterium.

* * * * *